United States Patent [19]

Inoue et al.

[11] Patent Number: 5,665,881
[45] Date of Patent: Sep. 9, 1997

[54] QUINOLINE COMPOUNDS

[75] Inventors: Yoshihisa Inoue; Hajime Ebisu; Naomichi Ishida; Norifumi Nakamura, all of Osaka; Jun Sasaki, Kanagawa; Takashi Okazoe, Kanagawa; Yoshitomi Morizawa, Kanagawa; Arata Yasuda, Kanagawa, all of Japan

[73] Assignees: The Green Cross Corporation, Osaka; Asahi Glass Co., Ltd., Tokyo, both of Japan

[21] Appl. No.: 541,965

[22] Filed: Oct. 10, 1995

Related U.S. Application Data

[62] Division of Ser. No. 55,873, May 4, 1993, Pat. No. 5,478,832.

[30] Foreign Application Priority Data

May 8, 1992 [JP] Japan ................................. 4-143407
Jun. 10, 1992 [JP] Japan ................................. 4-176188

[51] Int. Cl.$^6$ ................................. C07D 215/14
[52] U.S. Cl. ................................. 546/170
[58] Field of Search ................................. 546/170

[56] References Cited

U.S. PATENT DOCUMENTS 5,371,227 12/1994 Cremer ................................. 546/176

FOREIGN PATENT DOCUMENTS 2081537  4/1993  Canada .
0400974 12/1990 European Pat. Off. .
0540400  5/1993  European Pat. Off. .

Primary Examiner—Matthew V. Grumbling
Attorney, Agent, or Firm—Sughrue, Mion, Zinn, Macpeak & Seas

[57] ABSTRACT

A quinoline compound represented by the formula (1) or a salt thereof:

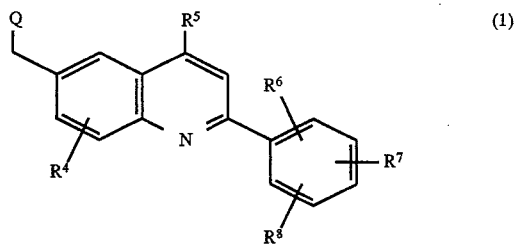

wherein the definition of each substituents are described in the specification, which have angiotensin II antagonism and hypotensive action and are useful as an agent for the prevention and treatment of cardiovascular system diseases such as hypertension, heart failure and the like.

8 Claims, No Drawings

QUINOLINE COMPOUNDS

This is a division of 08/055,873 filed May 4, 1993, now U.S. Pat. No. 5,478,832.

FIELD OF THE INVENTION

The present invention relates to novel quinoline compounds and salts thereof having excellent pharmacological activities. More specifically, it relates to novel quinoline compounds, and salts thereof which have angiotensin II antagonist and hypotensive activities and which are useful as agents for the prevention and the treatment of cardiovascular system diseases, such as hypertension.

BACKGROUND OF THE INVENTION

Blood pressure in the living body is controlled mainly by the sympathetic nervous system and the balance of pressor and depressor systems. The renin-angiotensin system is a pressor system. In the renin-angiotensin system, renin acts on angiotensinogen to form angiotensin I which is subsequently converted into angiotensin II by the action of an angiotensin converting enzyme. Angiotensin II shows strong angiotonic activity and acts on the adrenal cortex to enhance secretion of aldosterone, thus increasing the blood pressure. Since angiotensin II exerts its function through the angiotensin II receptor located on the cell membrane, its antagonist can be used, in addition to an angiotensin converting enzyme inhibitor, as a therapeutic agent for the treatment of hypertension caused by angiotensin II.

Angiotensin II antagonist peptides such as saralasin are known in the art. However, peptides are not effective when administered orally. Recently, non-peptide angiotensin II antagonists have been reported, for example, in JP-A-56-71074, PCT Application published in Japan No. 3-501020, JP-A-3-95181, JP-A-3-236377 and JP-A-3-271288, and their efficacy by oral administration has been confirmed. (The term "JP-A" as used herein means an "unexamined published Japanese patent application")

SUMMARY OF THE INVENTION

An object of the present invention is to provide a non-peptide compound which has excellent angiotensin II antagonist activity and remains effective when administered orally.

As a result of intensive studies to attain the above object, it has been found that a novel quinoline compound represented by formula (1) or a salt thereof has excellent angiotensin II antagonist activity and remains effective when administered orally.

Thus, the present invention provides a quinoline compound represented by the following formula (1) or a salt thereof:

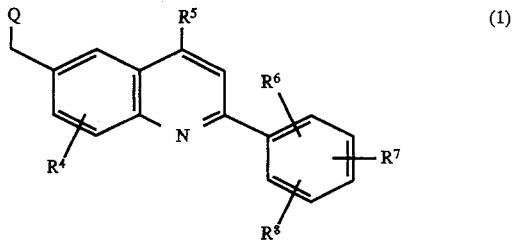

(1)

wherein Q is a heterocyclic derivative moiety represented by formulae (2) or (3)

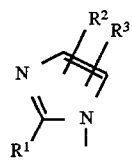

(2)

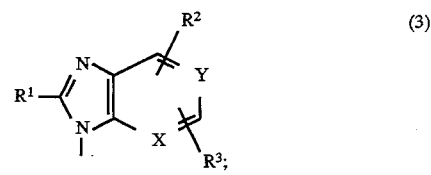

(3)

wherein $R^1$ is a lower alkyl, halo lower alkyl, cyclo lower alkyl, alkenyl, alkoxy, alkoxy lower alkyl or alkylthio group;

$R^2$ and $R^3$ may be the same or different and each represents hydrogen or halogen atom, a lower alkyl, halo lower alkyl, cyclo lower alkyl, alkenyl or alkoxy group, $C_mF_{2m+1}$—, —$(CH_2)_nR^9$ or —$(CH_2)_pCOR^{10}$;

$R^4$ is a hydrogen or halogen atom, a lower alkyl or alkoxy group or $C_mF_{2m+1}$—;

$R^5$ is a hydrogen atom or a group selected from —COOH, —$COOR^{11}$, —$CONH_2$ and —CN;

$R^6$ is a group selected from —COOH, —$COOR^{12}$, —$CONH_2$, —CN and —$NHSO_2CF_3$ or C-bonding tetrazolyl group;

$R^7$ and $R^8$ may be the same or different and each represents a hydrogen or halogen atom, a lower alkyl or alkoxy group, or $C_mF_{2m+1}$—;

X and Y may be the same or different and each represents CH or a nitrogen atom;

$R^9$ is a hydroxy or alkoxy group;

$R^{10}$ is a hydrogen atom or a hydroxy, lower alkyl or alkoxy group;

$R^{11}$ and $R^{12}$ may be the same or different and each represents a lower alkyl, alkenyl, cyclo lower alkyl, aryl or aralkyl group;

m is an integer of 1 to 6;

n is an integer of 1 to 4; and p is an integer of 0 to 4.

The present invention also provides a process for the production of the quinoline compound represented by formula (1) or a salt thereof which comprises reacting a compound represented by formula (4) with a compound represented by formulae ( 5 ) or ( 6 ):

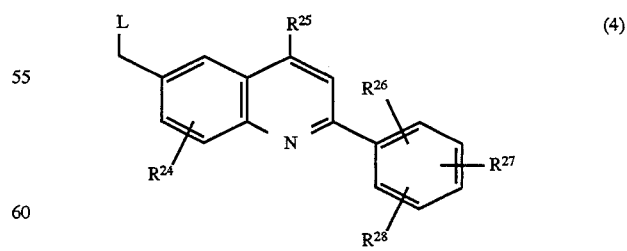

(4)

wherein L is a leaving group and $R^{24}$, $R^{25}$, $R^{26}$, $R^{27}$ and $R^{28}$ are the same groups respectively corresponding to $R^4$, $R^5$, $R^6$, $R^7$ and $R^8$ shown in formula (1) or represent groups which can be converted into corresponding groups $R^4$, $R^5$, $R^6$, $R^7$ and $R^8$;

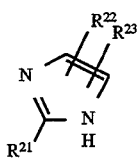

wherein $R^{21}$, $R^{22}$ and $R^{23}$ are the same groups respectively corresponding to $R^1$, $R^2$ and $R^3$ shown in formula (2) or groups which can be converted into corresponding groups $R^1$, $R^2$ and $R^3$; and

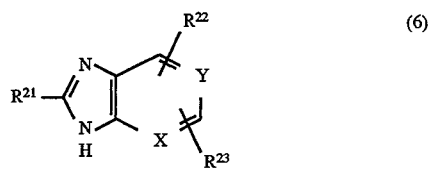

wherein $R^{21}$, $R^{22}$ and $R^{23}$ are the same groups respectively corresponding to $R^1$, $R^2$ and $R^3$ shown in formula (3) or represent groups which can be converted into corresponding groups $R^1$, $R^2$ and $R^3$. X and Y are the same as defined for formula (3).

The present invention further provides a pharmaceutical composition which comprises the quinoline compound represented by formula (1) or a salt thereof and a pharmaceutically acceptable carrier, an angiotensin II antagonist, as well as a drug for use in the prevention and treatment of cardiovascular system diseases (especially hypertension and heart failure), which comprises the quinoline compound represented by formula (1) or a salt thereof as the active ingredient.

DETAILED DESCRIPTION OF THE INVENTION

The term "lower" as used herein with regard to organic groups means that each group has 1 to 6 carbon atoms. The lower alkyl groups in relation to $R^1$ to $R^4$, $R^7$, $R^8$ and $R^{10}$ to $R^{12}$ may be linear or branched, with typical examples including methyl, ethyl, propyl, isopropyl, butyl, isobutyl, t-butyl, pentyl and hexyl groups.

The halo lower alkyl groups listed for $R^1$ to $R^3$ are lower alkyl groups substituted with halogens (fluorine, chlorine, bromine and iodine), which may be linear or branched, with typical examples including chloromethyl, 2-chloroethyl, bromomethyl, 2-bromoethyl, 1,2-dichloroethyl, 1,2-dibromoethyl and 3-trifluoromethylpropyl groups.

The cyclo lower alkyl groups listed for $R^1$ to $R^3$, $R^{11}$ and $R^{12}$ are cycloalkyl groups having 3 to 6 carbon atoms which constitute the ring, with typical examples including cyclopropyl, cyclobutyl, cyclopentyl and cyclohexyl groups.

The alkenyl groups listed for $R^1$ to $R^3$, $R^{11}$ and $R^{12}$ are preferably lower alkenyl groups, more preferably those having 2 to 4 carbon atoms, which may be linear or branched, with typical examples including vinyl, allyl, 1-propenyl, isopropenyl and 1-butenyl groups.

The alkoxy groups listed for $R^1$ to $R^4$ and $R^7$ to $R^{10}$ are preferably lower alkoxy groups, more preferably those having 1 to 4 carbon atoms, which may be linear or branched, with typical examples including methoxy, ethoxy, propoxy and butoxy groups.

The alkoxy lower alkyl groups listed for $R^1$ may be linear or branched, preferably having a lower alkoxy group as the alkoxy moiety, with typical examples including methoxyethyl, 3-methoxypropyl and 2-ethoxyethyl groups.

The alkylthio groups listed for $R^1$ are preferably lower alkylthio groups, more preferably those having 1 to 4 carbon atoms, which may be linear or branched, with typical examples including methylthio, ethylthio, propylthio and butylthio groups.

The halogen atoms listed for $R^2$ to $R^4$, $R^7$ and $R^8$ include fluorine, chlorine, bromine and iodine.

The aryl groups listed for $R^{11}$ and $R^{12}$ are monovalent aromatic hydrocarbon radicals which may have substituents such as a halogen atom, a lower alkoxy group, a lower alkylamino group and the like, and are preferably a phenyl group or its derivatives, with typical examples including phenyl, tolyl, p-halophenyl (e.g. p-chlorophenyl, p-bromophenyl, etc.), alkoxyphenyl (e.g. methoxyphenyl, ethoxyphenyl, etc.) and dialkylaminophenyl (e.g. dimethylaminophenyl, diethylaminophenyl, etc.) groups.

The aralkyl groups listed for $R^{11}$ and $R^{12}$ are lower alkyl groups substituted with aryl groups, in which the aryl groups as the substituents are those described above and the alkyl groups may preferably have 1 to 4 carbon atoms, with typical examples including benzyl, benzhydryl, trityl and phenetyl groups.

Examples of the leaving group represented by L include chlorine, bromine, iodine, a methanesulfonyloxy group and a p-toluenesulfonyloxy group.

The groups listed for $R^{21}$ to $R^{28}$ which can be converted into $R^1$ to $R^8$ are those groups which are only different from the groups $R^1$ to $R^8$ in that their functional groups are protected by protective groups, such as an amino group, a protected amino group, a mercapto group, a protected mercapto group and the like.

The positions of the substituents represented by $R^2$ to $R^4$ and $R^6$ to $R^8$ in formulae (1), (2) and (3) are not particularly limited, but preferably $R^6$ may be in an ortho position in relation to the bonding position.

The same applies to the positions of the $R^{22}$ to $R^{24}$ and $R^{26}$ to $R^{28}$ substituents listed in formulae (4), (5) and (6).

Preferred examples of the quinoline compound as represented by formula (1) are those compounds in which Q is a heterocyclic derivative represented by formula (2), wherein $R^1$ is a lower alkyl group or an alkenyl group, $R^2$ is a chlorine atom and $R^3$ is the group —$(CH_2)_n R^9$ or —$(CH_2)_p COR^{10}$, wherein $R^9$ is a hydroxy group or an alkoxy group, $R^{10}$ is a hydrogen atom, a hydroxy group or an alkoxy group, n is an integer of 1 to 4 and p is an integer of 0 to 4.

Also preferred are those compounds in which Q is a heterocyclic derivative represented by formula (3), wherein $R^1$ is a lower alkyl group or an alkenyl group, $R^2$ and $R^3$ may be the same or different and each represents a hydrogen atom, a halogen atom, a lower alkyl group, the group —$(CH_2)_n R^9$ or —$(CH_2)_p COR^{10}$, wherein $R^9$ is a hydroxy group or an alkoxy group, $R^{10}$ is a hydrogen atom, a hydroxy group or an alkoxy group, n is an integer of 1 to 4 and p is an integer of 0 to 4, X is a nitrogen atom, Y is CH, $R^4$ is a hydrogen atom, $R^5$ is a hydrogen atom, the group —COOH or $COOR^{11}$, wherein $R^{11}$ is a lower alkyl group, an alkenyl group, a cyclo lower alkyl group, an aryl group or an aralkyl group, $R^6$ is a group, —COOH or $COOR^{12}$, wherein $R^{12}$ is a lower alkyl group, an alkenyl group, a cyclo lower alkyl group, an aryl group or an aralkyl group, or a C-bonding tetrazolyl group and $R^7$ and $R^8$ may be the same or different and each represents a hydrogen atom, a fluorine atom, a chlorine atom, a lower alkyl group or an alkoxy group.

Particularly preferred examples of the quinoline compound represented by formula (1) are those compounds in which Q is a heterocyclic derivative represented by formula (2), wherein $R^1$ is a lower alkyl group, $R^2$ is a chlorine atom, $R^3$ is the group —$(CH_2)_nR^9$ or —$(CH_2)_pCOR^{10}$, wherein $R^9$ is a hydroxy group, $R^{10}$ is a hydrogen atom, a hydroxy group or an alkoxy group, n is 1 and p is 0 or 1, $R^4$ is a hydrogen atom, $R^5$ is a hydrogen atom, $R^6$ is a —COOH group or a C-bonding tetrazolyl group and $R^7$ and $R^8$ may be the same or different and each represents a hydrogen atom, a fluorine atom, a chlorine atom or a lower alkyl group.

Also particularly preferred are those compounds in which Q is a heterocyclic derivative represented by formula (3), wherein $R^1$ is a lower alkyl group, $R^2$ and $R^3$ may the same or different and each represents a hydrogen atom, a lower alkyl group, the group —$(CH_2)_nR^9$ or —$(CH_2)_pCOR^{10}$, wherein $R^9$ is a hydroxyl group, $R^{10}$ is a hydrogen atom, a hydroxy group or an alkoxy group, n is 1 and p is 0 or 1, $R^4$ is a hydrogen atom, $R^5$ is a hydrogen atom, $R^6$ is a —COOH group or a C-bonding tetrazolyl group, $R^7$ and $R^8$ may be the same or different and each represents a hydrogen atom, a fluorine atom, a chlorine atom and a lower alkyl group, X is a nitrogen atom and Y is CH.

When Q in formula (1) is a heterocyclic derivative represented by formula (3), substituents, $R^1$, $R^2$ and $R^3$ most preferably have 4 carbon atoms in total.

The quinoline compound (1) can be produced as exemplified by the following processes.

In a first process (A), compounds represented by formula (1) are mutually converted. In a second process (B), a compound similar to the compound represented by formula (1), for example, having different substituents but has the same molecular skeletal backbone is converted into the compound of formula (1). In a third process (C), the compound of formula (1) or an analogous compound thereto is synthesized by a reaction of two or more intermediate compounds, in which the analogous compound is further converted into the compound of formula (1) following the process (B). The process (C) relates to a framework formation reaction.

Illustrative examples of the process (A) are as follows.

A compound of formula (1) in which $R^5$ is —COOH and $R^6$ is —$COOR^{12}$, where $R^{12}$ is a lower alkyl group, an alkenyl group, a cyclo lower alkyl group, an aralkyl group or an aryl group, is obtained by hydrolyzing a compound of formula (1) in which $R^5$ is —$COOR^{11}$, where $R^{11}$ is a lower alkyl group, an alkenyl group, a cyclo lower alkyl group, an aralkyl group or an aryl group, with one equivalent of an alkali such as sodium hydroxide, potassium hydroxide or the like without exerting influence on $R^6$, —$COOR^{12}$, where $R^{12}$ is a lower alkyl group, an alkenyl group, a cyclo lower alkyl group or an aryl group.

A compound of formula (1) in which $R^5$ is a hydrogen atom is obtained by subjecting a compound of formula (1) in which $R^5$ is —COOH and $R^6$ is —$COOR^{12}$, where $R^{12}$ is a lower alkyl group, an alkenyl group, a cyclo lower alkyl group or an aryl group, to reflux in a solvent having a high boiling point, such as diphenyl ether, at a temperature around the boiling point of the solvent.

A compound of formula (1) in which $R^6$ is —COOH is obtained by hydrolyzing a compound of formula (1) in which $R^6$ is —$COOR^{12}$, where $R^{12}$ is a lower alkyl group, an alkenyl group, a cyclo lower alkyl group, an aralkyl group or an aryl group.

A compound of formula (1) in which $R^6$ is a C-bonding tetrazolyl group is obtained by allowing a compound of formula (1) in which $R^6$ is —CN to react with an appropriate azide compound such as sodium azide, ammonium azide which is preferably prepared from sodium azide and ammonium chloride immediately prior to use, tributyltin azide which is preferably prepared from sodium azide and tributyltin chloride immediately prior to use or the like, in an anhydrous solvent such as toluene, xylene, dimethoxyethane, tetrahydrofuran or the like at the reflux temperature of the solvent or a temperature close to the reflux temperature. When tributyltin azide is used, the resulting reaction product is treated with a basic or acidic aqueous solution to remove the tributyltin group.

The compound of formula (1) in which $R^6$ is a C-bonding tetrazolyl group is also obtained by converting —COOH of a compound of formula (1) in which $R^6$ is —COOH into an acid chloride or an active ester in accordance with the method of J. V. Duncia et al. (*J. Org. Chem.*, 56., 2395 (1991)) and then allowing the resulting product to react with 2-aminopropionitrile, followed by further reaction with triphenylphosphine, diethyl azodicarboxylate and trimethylsilylazide.

Typical examples of the process (B) is conversion of functional groups and substituents. For example, the compound represented by formula (1) can be obtained by converting a functional group or a substituent of an analogous compound having the same framework of the compound of formula (1), but with a different functional group or a substituent which is not included in formula (1). A typical example of the functional group conversion is deprotection of a functional group protected with a protective group. The compound of formula (1) can also be obtained by converting a protected functional group $R^6$ into $R^6$.

Illustrative examples of the process (B) are as follows.

A compound of formula (1) in which $R^6$ is a C-bonding tetrazolyl group is obtained by deprotecting a compound analogous to the compound of formula (1), a compound in which a position corresponding to $R^6$ has a C-bonding tetrazolyl group protected with an appropriate protective group. In this instance, preferred protective groups include a triphenylmethyl group, a cyanoethyl group and the like. The deprotection step may be effected by a common means such as the procedure reported by T. W. Greene ("Protective Groups in Organic Synthesis"; John Wiley and Sons Inc., 1981).

A compound of formula (1) in which $R^6$ is —$NHSO_2CF_3$ is obtained by reacting a compound analogous to the compound of formula (1), in which a position corresponding to $R^6$ has an amino group, with anhydrous trifluoromethane sulfonate in an appropriate solvent, such as dichloromethane, in the presence of an appropriate base such as triethylamine.

The compound analogous to the compound of formula (1) in which a position corresponding to $R^6$ has an amino group can be obtained by subjecting a compound of formula (1) in which $R^6$ is —COOH, if necessary after protecting other functional groups with an appropriate protecting group, to Curtius Rearrangement Reaction using diphenylphosphoryl azide in an alcohol solvent such as t-butyl alcohol in the presence of a base such as triethylamine, thereby preparing a carbamate, and then carrying out acid hydrolysis of the resulting product with hydrochloric acid in an appropriate solvent such as ethanol or the like.

The process (C) is accompanied by a framework formation reaction to obtain the compound represented by formula (1) and its analogous compounds. A typical example of the framework formation reaction is a reaction of a compound represented by the following formula (4) with another compound represented by the following formula (5) or (6).

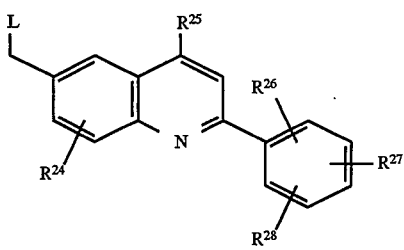

wherein, L and $R^{24}$ to $R^{25}$ are as defined above.

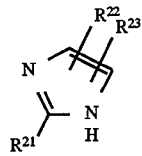

wherein $R^{21}$ to $R^{23}$ are as defined above.

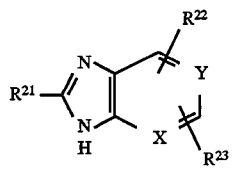

wherein L and $R^{21}$ to $R^{23}$ are as defined above.

The framework of the quinoline compound represented by formula (1) is formed by reacting a compound represented by formula (4) with one of the imidazoles represented by formula (5) or one of the imidazopyridines represented by formula (6) in an aprotic solvent (e.g. N,N-dimethylformamide, N,N-dimethylacetamide, tetrahydrofuran, dioxane or the like) in the presence of a base, such as sodium hydride, sodium carbonate, potassium carbonate, sodium methoxide or the like, at a temperature in the range of from 0° C. to the reflux temperature of the used solvent.

During the process of synthesis of the quinoline compound (1), $R^1$ to $R^8$ are not necessarily maintained as the same groups during the progression from the starting material to the final product. In some cases, it is necessary to obtain the final product by carrying out a conversion reaction as illustrated below.

The following describes examples of the process (C) which uses an intermediate compound analogous to the compound of formula (1) in which $R^{21}$ to $R^{28}$, except for $R^{26}$, are the same respectively as the corresponding $R^1$ to $R^8$, except for $R^6$, of formula (1).

A quinoline compound (1) in which $R^6$ is a C-bonding tetrazolyl group is obtained by reacting a compound represented by formula (4), in which $R^{26}$ is a protected C-bonding tetrazolyl group, with one of the imidazoles represented by formula (5) or one of the imidazopyridines represented by formula (6) in an aprotic solvent (e.g. N,N-dimethylformamide, N,N-dimethylacetamide, tetrahydrofuran, dioxane or the like) in the presence of a base, such as sodium hydride, sodium carbonate, potassium carbonate, sodium methoxide or the like, at a temperature in the range of from 0° C. to the reflux temperature of the used solvent.

It also may be obtained by reacting a compound represented by formula (4), in which $R^{26}$ is a protected C-bonding tetrazolyl group, with one of the imidazoles represented by formula (5) or one of imidazopyridines represented by formula (6) in a mixture solvent consisting of a basic aqueous solution (e.g. sodium hydroxide aqueous solution, potassium hydroxide aqueous solution or the like) and an appropriate organic solvent, such as methylene chloride or the like, in the presence of a phase-transfer catalyst such as a tetraalkylammonium salt (e.g. "Aliquat 336") at a temperature in the range of from 0° C. to the reflux temperature of the solvent used.

The intermediate compound represented by the formula (4) can be obtained, for example, by converting the 6-position methyl group of a compound represented by the following formula (7) into —CH$_2$L, where L is a leaving group as defined above.

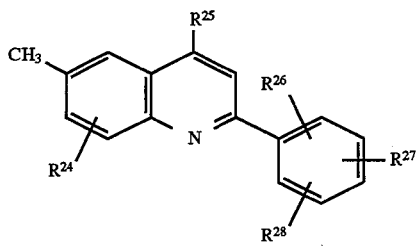

wherein $R^{24}$ to $R^{28}$ are as defined above.

Though the substituents in formula (7) are the same as those in formula (4) in this case (that is, $R^{24}$ to $R^{28}$ are common in both formulae), other substituents may also be used provided that they can be converted into corresponding $R^4$ to $R^8$ in formula (1). Also, the following formulae (8) and (9) are described in the same manner based on the assumption that their substituents are the same as those in formula (4).

For example, when L is chlorine, bromine or iodine, the compound represented by formula (7) can be converted into the compound of formula (4) by reacting the compound (7) with N-chlorosuccinimide, N-bromosuccinimide or N-iodosuccinimide in the presence of a radical initiator such as azobisisobutyro-nitrile, dibenzoyl peroxide or the like. The same reaction can also be effected by means of light irradiation, e.g. UV irradiation, instead of the use of the radical initiator.

A compound represented by formula (7) in which $R^{25}$ is —COOH can be obtained by mixing a compound represented by the following formula (8) with a compound represented by the following formula (9), and subjecting the mixture to reflux in an appropriate alkali aqueous solution such as of sodium hydroxide, potassium hydroxide or the like.

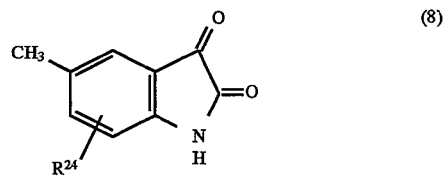

wherein $R^{24}$ is as defined above.

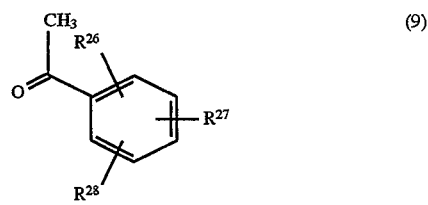

wherein $R^{26}$ to $R^{28}$ are as defined above.

A compound represented by formula (7) in which $R^{25}$ is a hydrogen atom can be synthesized, for example, by subjecting a compound represented by formula (7) in which $R^{25}$ is —COOH to reflux in a high boiling point solvent, such as diphenyl ether, at a temperature around the boiling point of the solvent, thereby effecting conversion of the substituent.

A compound represented by the formula (7) in which $R^{25}$ is —COOR$^{11}$ and $R^{26}$ is —COOR$^{12}$ can be obtained, for example, by allowing a compound represented by the formula (7) in which $R^{25}$ and $R^{26}$ are both —COOH to react with thionyl chloride in methanol, thereby effecting conversion of the substituents into —COOR$^{11}$ and —COOR$^{12}$ wherein $R^{11}$ and $R^{12}$ are methyl groups.

A compound represented by formula (7) in which $R^{25}$ is —COOH and $R^{26}$ is —COOR$^{12}$ can be obtained, for example, by subjecting a compound represented by formula (7) in which $R^{25}$ is —COOR$^{11}$ and $R^{26}$ is —COOR$^{12}$ to hydrolysis with one equivalent amount of an alkali such as sodium hydroxide, potassium hydroxide or the like in a methanol/water mixture solvent, thereby effecting conversion of only the $R^{25}$ substituent.

A compound represented by formula (7) in which $R^{26}$ is a C-bonding tetrazolyl group protected with an appropriate protective group such as triphenylmethyl group, cyanoethyl group or the like can be prepared from another compound represented by formula (7) in which $R^{26}$ is —CN by converting the substituent. For example, such a compound is obtained by reacting the compound (7) in which $R^{26}$ is —CN with an appropriate azide compound such as sodium azide, ammonium azide which is preferably prepared from sodium azide and ammonium chloride immediately prior to use, tributyltin azide which is preferably prepared from sodium azide and tributyltin chloride immediately prior to use or the like, in an anhydrous solvent such as toluene, xylene, dimethoxyethane, tetrahydrofuran or the like at the reflux temperature of the solvent or a temperature close to the reflux temperature, thereafter effecting addition of a protective group. When tributyltin azide is used, the resulting product is treated with a basic or acidic aqueous solution to remove the tributyltin group.

Alternatively, the compound represented by formula (7) in which $R^{26}$ is a C-bonding tetrazolyl group protected with an appropriate protective group such as triphenylmethyl group, cyanoethyl group or the like can be obtained by converting —COOH of a compound represented by formula (7) in which $R^{26}$ is —COOH into an acid chloride or an active ester in accordance with the method of J. V. Duncia et al. (*J. Org. Chem.*, 56, 2395 (1991)) and then reacting the resulting product with 2-aminopropionitrile, followed by further reaction with triphenylphosphine, diethyl azodicarboxylate and trimethylsilylazide.

A compound of formula (7) in which $R^{26}$ is an amino group having a protecting group can be obtained by subjecting another compound of formula (7) in which $R^{26}$ is —COOH to Curtius rearrangement using diphenylphospholyl azide in an alcohol solvent such as t-butyl alcohol in the presence of a base such as triethylamine. In this case, the protecting group of the amino group is a carbamate such as t-butyl carbamate or the like.

The imidazoles represented by formula (5) can be synthesized, for example, in accordance with the method disclosed in JP-A-3-501020 and modifying the procedure, if necessary.

Also, the imidazopyridines represented by the formula (6) can be synthesized, for example, in accordance with the method disclosed in JP-A-3-95181 and modifying the procedure, if necessary.

The quinoline compound (1) of the present invention can be isolated and purified by known means such as extraction, crystallization, fractional crystallization, recrystallization, chromatography and the like.

The thus obtained quinoline compound (1) can be converted into its salt in a customary manner known in the field.

Examples of the salt of the quinoline compound (1) are acid addition salts derived from the quinoline compound and inorganic or organic acids. Illustrative examples of such salts include hydrochloride, hydrobromate, sulfate, phosphate, methanesulfonate, p-toluenesulfonate, oxalate, tartarate, citrate, maleate, fumarate, succinate, lactate, glutarate, acetate, trifluoroacetate and the like, as well as various amino acid salts.

Also useful as the salt of the quinoline compound (1) are those formed from the quinoline compound and bases which include for example: alkali metals such as sodium, potassium and the like; alkaline earth metals such as calcium, magnesium and the like; and ammonium and substituted ammonium compounds such as dimethylammonium, triethylammonium and the like.

The quinoline compound (1) of the present invention and salts thereof display excellent angiotensin II antagonism with low toxicity. Thus, the quinoline compound (1) of the present invention is useful as an angiotensin II antagonist for the treatment or prevention of angiotensin II-mediated cardiovascular system diseases such as hypertension (e.g. essential hypertension, renal hypertension, etc.), heart failure and the like.

Also, it is expected that the quinoline compound (1) of the present invention and salts thereof can be applied to pharmaceutical drugs for the treatment and/or prevention of heart disturbances such as angina pectoris, arrhythmia, myocardial infarction and the like, as well as of aldosteronism, cerebral circulation diseases, senile dementia and eye diseases such as glaucoma and the like. The compound is also expected to be useful as a diagnostic agent for the tests of the renin-angiotensin system.

When used for the treatment or prevention of diseases, the quinoline compound (1) of the present invention or a salt thereof may be prepared into any of the commonly used pharmaceutical preparations by mixing the formula (1) compound or its salt of the present invention as an active ingredient with pharmaceutically acceptable carriers, such as organic or inorganic solids or liquid fillers suitable for oral or parenteral administration or external use. The pharmaceutical preparation may be used in solid dosage forms, such as tablets, granules, powders, capsules and the like or in liquid forms, such as solutions, suspensions, syrups, emulsions, and the like.

If necessary, the above pharmaceutical preparation may be further blended with adjuvants, stabilizing agents, moistening agents and other known additives, such as lactose, citric acid, tartaric acid, stearic acid, magnesium stearate, China clay, sucrose, corn starch, talc, gelatin, agar, pectin, peanut oil, olive oil, cacao oil, ethylene glycol and the like.

The quinoline compound (1) or its salt can be administered to mammals including human. The dosage of the quinoline compound (1) or its salt varies depends on the age of the patient, types and symptoms of diseases to be prevented/treated and type of the quinoline compound (1) or its salt to be applied, but generally may be administered to a human patient in a dose of from 0.01 to about 500 mg per day. The quinoline compound (1) or its salt may be used in an average amount per one dose of about 0.05 to 100 mg.

The following examples are provided to further illustrate the present invention. It is to be understood, however, that the examples are for the purpose of illustration only and are not intended as a definition of the limits of the present invention.

REFERENCE EXAMPLE 1

Synthesis of 5-methylisatin

An aqueous solution (222 ml) containing 16.7 g (0.10 mol) of chloral hydrate was mixed with 243 g of sodium sulfate, an aqueous solution (56.0 ml) containing 10.0 g (93.3 mmol) of p-toluidine and 9.56 of concentrated hydrochloric acid and an aqueous solution (242 ml) containing 20.5 g (0.29 mol) of hydroxylamine hydrochloride in this order and the resulting mixture was heated under reflux with stirring for 30 minutes. After cooling to room temperature, the mixture was filtered with suction to collect the yellowish brown precipitate. The precipitate was dissolved in 500 ml of a 1.5N sodium hydroxide solution and neutralized with 2M hydrochloric acid. The resulting mixture was filtered and the filtrate was acidified with 2M hydrochloric acid. The thus precipitated isonitroso compound was collected by filtration and washed with iced water followed by drying. The dried product was added to 62 g of concentrated sulfuric acid which had been heated to 60° C. over 40 minutes and the mixture was further heated at 75° C. for 10 minutes. After cooling to room temperature, the resulting mixture was poured into 160 ml of iced water followed by filtration to obtain 10.0 g of 5-methylisatin.

NMR (270 MHz, Acetone-$d_6$):

$\delta$9.9 (bs,1H); 6.9–7.5 (m, 3H); 2.3 (s, 3H)

REFERENCE EXAMPLE 2

Synthesis of 2-(2-carboxyphenyl)-6-methyl-4-quinoline-carboxylic acid

To 9.93 ml of water were added 10.0 g (62.1 mmol) of 5-methylisatin obtained in Reference Example 1 and 4.96 g (0.12 mol) of sodium hydroxide. 10.2 g (62.1 mmol) of 2-acetyl benzoate was further added thereto and the mixture was heated to 90° C. under reflux. The mixture was further heated at 115° C. for one hour after the reaction became mild. Thereafter, the mixture was allowed to cool to room temperature and poured into 200 g of iced water. The aqueous layer was washed with ether and acidified with 2M hydrochloric acid. The formed precipitate was collected by filtration to obtain 6.55 g of 2-(2-carboxyphenyl)-6-methyl-4-quinolinecarboxylic acid.

NMR (270 MHz, Acetone-$d_6$):

$\delta$7.70–8.70 (m, 8H); 2.66 (s, 3H)

REFERENCE EXAMPLE 3

Synthesis of methyl 2-(2-methoxycarbonylphenyl)-6-methyl-4-quinolinecarboxylate 2.77 g (9.03 mmol) of 2-(2-carboxyphenyl)-6-methyl-4-quinolinecarboxylic acid obtained in Reference Example 2 was suspended in 10 ml of methanol. 1.3 ml (18 mmol) of thionyl chloride were added thereto with maintaining the mixture at −10° C. and the mixture was stirred for 24 hours. After concentrated under reduced pressure, the residue was purified by flash silica gel chromatography using chloroform to obtain 377 mg of methyl 2-(2-methoxycarbonylphenyl)-6-methyl-4-quinolinecarboxylate.

NMR (270 MHz, CDCl$_3$):

$\delta$7.49–8.56 (m, 8H); 4.04 (s, 3H); 3.62 (s, 3H); 2.60 (s, 3H)

REFERENCE EXAMPLE 4

Synthesis of 2-(2-methoxycarbonylphenyl)-6-methyl-4-quinolinecarboxylic acid In 2 ml of methanol were dissolved 377 mg (1.23 mmol) of methyl 2-(2-methoxycarbonylphenyl)-6-methyl-4-quinoline-carboxylate obtained in Reference Example 3 and 49 mg (1.2 mmol) of sodium hydroxide. 3 ml of water were added thereto and the resulting mixture was stirred for 24 hours. After concentrated under reduced pressure, water was added to the residue, the aqueous layer was acidified and extracted with ethyl acetate. The organic layer was dried over magnesium sulfate followed by distillation under reduced pressure. The resulting residue was purified by flash silica gel chromatography using a mixed solvent of chloroform and methanol (70/1) to obtain 267 mg of 2-(2-methoxycarbonyl-phenyl)-6-methyl-4-quinolinecarboxylic acid.

NMR (270 MHz, CD$_3$OD):

$\delta$7.70–8.58 (m, 8H); 3.60 (s, 3H); 2.59 (s, 3H)

REFERENCE EXAMPLE 5

Synthesis of methyl 2-(6-methylquinolin-2-yl) benzoate 267 mg (0.831 mmol) of 2-(2-methoxycarbonylphenyl)-6-methyl-4-quinolinecarboxylic acid obtained in Reference Example 4 were dissolved in 4.0 ml of diphenyl ether and heated at 225° C. for 10 minutes. After allowing the mixture to cool to room temperature, purification was carried out by flash silica gel chromatography using a mixed solvent of hexane and ethyl acetate (10/1) to obtain 154 mg of methyl 2-(6-methylquinolin-2-yl)benzoate.

NMR (270 MHz, CDCl$_3$):

$\delta$7.47–8.13 (m, 9H); 3.63 (s, 3H); 2.56 (s, 3H)

REFERENCE EXAMPLE 6

Synthesis of 2-(6-methylquinolin-2-yl)benzoic acid 7.08 g (25.5 mmol) of methyl 2-(6-methylquinolin-2-yl) benzoate obtained in Reference Example 5 were suspended in 75 ml of methanol and then 35 ml of water in which 3.06 g (76.6 mmol) of sodium hydroxide were dissolved were added thereto. After heating at 60° C for 3 hours, the reaction mixture was concentrated under reduced pressure and 200 ml of water were added to the residue. The resulting solution was acidified with 2N hydrochloric acid and the thus formed precipitate Was collected by filtration. The precipitate was washed with water and dried to obtain 2-(6-methylquinolin-2-yl)-benzoic acid.

NMR (270 MHz, CD$_3$OD):

$\delta$7.6–8.3 (m, 9H); 2.58 (s, 3H)

REFERENCE EXAMPLE 7

Synthesis of 2-(6-methylquinolin-2-yl)benzamide

To 2.47 g (9.38 mmol) of 2-(6-methylquinolin-2-yl)-benzoic acid obtained in Reference Example 6 were added 30 ml of toluene. To the resulting suspension were added 1.37 ml (18.76 mmol) of thionyl chloride and one drop of dimethylformamide. After heating under reflux for 3 hours, the mixture was allowed to cool to room temperature. The solid material was collected by filtration and washed three times with 10 ml portion of toluene followed by drying. The thus obtained solid was added to 30 ml of iced concentrated aqueous ammonia with vigorous stirring and the temperature of the solution was maintained so as not to exceed 15° C. After the mixture was stirred overnight at room temperature, 30 ml of water was added thereto, the solid material was collected by filtration and was washed three times with 20 ml portions of water. The filter cake was suspended in diethyl ether, collected by filtration and dried to obtain 2.05 g of 2-(6-methylquinolin-2-yl)benzamide.

NMR (270 MHz, CDCl$_3$):

δ7.5–8.2 (m, 9H); 6.4 (bs, 1H); 5.6 (bs, 1H); 2.58 (s, 3H)

REFERENCE EXAMPLE 8

Synthesis of 2-(6-methylquinolin-2-yl)benzonitrile 15 ml of pyridne were added to 2.05 g (7.82 mmol) of 2-(6-methylquinolin-2-yl)benzamide obtained in Reference Example 7 and the mixture was stirred. Were, 1.49 g (7.82 mmol) of p-toluenesulfonyl chloride were added thereto and stirred at room temperature for 2 hours. After further stirring the mixture at 40° C. for 2 hours, the reaction mixture was poured into 30 ml of water and extracted with 50 ml of methylene chloride. The resulting extract was dried over magnesium sulfate followed by filtration. The filtrate was concentrated and the concentrate was subjected to silica gel chromatography using a mixed solvent of hexane and ethyl acetate (7/1) to obtain 0.86 g of 2-(6-methylquinolin-2-yl) benzonitrile.

NMR (270 MHz, CDCl$_3$):

δ7.5–8.2 (m, 9H); 2.58 (s, 3H)

REFERENCE EXAMPLE 9

Synthesis of 5-[2-(6-methylquinolin-2-yl)phenyl]-2-triphenyl-methyl-2H-tetrazole 3.5 ml of toluene were added to 855 mg (3.5 mmol) of 2-(6-methyl-quinolin-2-yl)benzonitrile obtained in Reference Example 8. To the mixture were further added 0.24 g (0.68 mmol) of sodium azide and 1 ml (3.83 mmol) of tributyltin chloride. After heating under reflux for 45 hours, the mixture was allowed to cool and diluted with 7 ml of toluene. To the mixture were added 0.4 ml (4 mmol) of a 10 N sodium hydroxide aqueous solution and 1.01 g (3.61 mmol) of tritylchloride with stirring. After stirring at room temperature for 1.5 hours, 15 ml of hexane were added to the mixture and the solid material was collected by filtration. The thus obtained solid material was washed with 10 ml of water twice and then 5 mls of methanol three times. The filter cake was dried under vacuum to obtain 1.36 g of 5-[2-(6-methylquinolin-2-yl)phenyl]-2-triphenylmethyl-2H-tetrazole.

NMR (270 MHz, CDCl$_3$):

δ6.8–8.1 (m, 24H); 2.54 (s, 3H)

REFERENCE EXAMPLE 10

Synthesis of 2-(4-chloro-6-methylquinolin-2-yl) benzonitrile 2.5 ml (34.2 mmol) of thionyl chloride were added to 1.28 g (4.88 mmol) of 2-(6-methylquinolin-2-yl)benzamide obtained in Reference Example 7 and the mixture was stirred. After heating the mixture under reflux for 3 hours, thionyl chloride was distilled off. The residue was dissolved in 100 ml of chloroform and poured into iced water. The organic layer was separated, neutralized with 150 ml of a saturated sodium bicarbonate solution, washed with a saturated sodium chloride solution and dried over magnesium sulfate followed by filtration. The resulting filtrate was concentrated and the concentrate was subjected to silica gel chromatography using a mixed solvent of hexane and ethyl acetate (10/1) to obtain 150 mg of 2-(4-chloro-6-methylquinolin-2-yl)benzo-nitrile.

NMR (270 MHz, CDCl$_3$):

δ7.5–8.1 (m, 8H); 2.62 (s, 3H)

REFERENCE EXAMPLE 11

Synthesis of 5-[2-(4-chloro-6-methylquinolin-2-yl) phenyl]-2-(triphenylmethyl)-2H-tetrazole 290 mg of 2-(4-chloro-6-methylquinolin-2-yl)benzonitrile obtained in Reference Example 10 was treated in the same manner as in Reference Example 9 to obtain 133 mg of 5-[2-(4-chloro-6-methylquinolin-2-yl)phenyl]-2-(triphenylmethyl)-2H-tetrazole.

NMR (270 MHz, CDCl$_3$):

δ6.8–8.2 (m, 23H); 2.6 (s, 3H)

EXAMPLE 1

Synthesis of methyl 2-{6-[(2-butyl-4-chloro-5-formyl-1H-imidazol-1-yl)methyl]quinolin-2-yl}benzoate 4 ml of carbon tetrachloride were added to 57.7 mg (2.08 mmol) of methyl 2-(6-methylquinolin-2-yl)benzoate obtained in Reference Example 5. To the mixture were further added 37.1 mg (2.08 mmol) of N-bromosuccinimide and 17 mg of (0.10 mmol) of azoisobutyronitrile followed by heating under reflux for one hour. After the mixture was concentrated under reduced pressure, the residue was dissolved in dichloromethane and washed with water. An organic layer was dried over magnesium sulfate and filtered to obtain a filtrate. The filtrate was concentrated under reduced pressure and the residue was dissolved in 10 ml of N,N-dimethylformamide. To the mixture were added 311 mg (1.67 mmol) of 2-butyl-4-chloro-1H-imidazol-5-carbaldehyde and 254 mg of (1.84 mmol) of potassium carbonate. Then, the mixture was stirred at room temperature for 24 hours.

The resulting reaction mixture was filtered and the filtrate was concentrated under reduced pressure. The residue was purified by flash silica gel chromatography using a mixed solvent of hexane and ethyl acetate (5/1 to 2/1) to obtain 627 mg of methyl 2-{6-[(2-butyl-4-chloro-5-formyl-1H-imidazol-1-yl)methyl]quinolin-2-yl}benzoate.

NMR (270 MHz, CDCl$_3$):

δ9.80 (s, 1H); 7.26–8.14 (m, 9H); 5.75 (s, 2H); 3.64 (s, 3H); 2.69 (t, J=8.3Hz, 2H); 1.69 (m, 2H); 1.38 (m, 2H);.0.88 (t, J=7.3Hz, 3H)

EXAMPLE 2

Synthesis of sodium 2-{6-[(2-butyl-4-chloro-5-formyl-1H-imidazol-1-yl)methyl]quinolin-2-yl}benzoate 186 mg (0.403 mmol) of methyl 2-{6-[(2-butyl-4-chloro-5-formyl-1H-imidazol-1-yl)methyl]quinolin-2-yl}benzoate obtained in Example 1 was mixed with 19.3 mg (0.484 mmol) of sodium hydroxide, 1 ml of water and 2 ml of ethanol and the mixture was stirred at room temperature for 24 hours. Then, the mixture was concentrated under reduced pressure and the concentrate was partitioned between water and ether. The aqueous layer was acidified with 1N hydrochloric acid and extracted with ethyl acetate. The organic layer was dried over magnesium sulfate followed by filtration. The resulting filtrate was concentrated under reduced pressure to obtain 142 mg of 2-{6-[(2-butyl-4-chloro-5-formyl-1H-imidazol-1-yl)methyl]quinolin-2-yl}benzoic acid.

A 1N sodium hydroxide solution was added to the thus obtained product in an equivalent amount (0.319 mmol) to dissolve the product. The resulting solution was lyophilized to obtain 149 mg of sodium 2-{6-[(2-butyl-4-chloro-5-formyl-1H-imidazol-1-yl)methyl]quinolin-2-yl}benzoate.
NNR (270 MHz, D$_2$O):

δ9.6 (s, 1H); 7.5–8.2 (m, 9H); 5.7 (s, 2H); 2.7 (t, J=8Hz, 2H); 1.5 (m, 2H); 1.2 (m, 2H); 0.8 (t, J=7 Hz, 3H)

EXAMPLE 3

Synthesis of methyl 2-{6-[(2-butyl-4-chloro-5-hydroxymethyl-1H-imidazol-1-yl)methyl]quinolin-1-yl}benzoate 440 mg (0.953 mmol) of methyl 2-{6-[(2-butyl-4-chloro-5-formyl-1H-imidazol-1-yl)methyl]quinolin-2-yl}benzoate obtained in Example 1 were dissolved in a mixed solvent of 10 ml of tetrahydrofuran and 10 ml of methanol and the mixture was stirred. 40 mg (1.0 mmol) of sodium borohydride were added thereto and allowed to react at room temperature for one hour. After the reaction mixture was concentrated under reduced pressure, dichloromethane was added to the residue and the mixture was washed with a saturated sodium chloride solution. The organic layer was dried over magnesium sulfate followed by filtration. The filtrate was concentrated under reduced pressure to obtain 368 mg of methyl 2-{6,[(2-butyl-4-chloro-5-hydroxymethyl-1H-imidazol-1-yl)methyl]quinolin-2-yl}benzoate.
NMR (270 MHz, CDCl$_3$):

δ8.1–7.3 (m, 9H); 5.4 (s, 2H); 4.5 (d, J=5Hz, 2H); 3.6 (s, 3H); 2.8 (t, J=8 Hz, 2H); 2.4 (t, J=3 Hz, 1H); 1.7 (m, 2H); 1.3 (m, 2H); 0.8 (t, J=7 Hz, 3H)

EXAMPLE 4

Synthesis of sodium 2-{6-[(2-butyl-4-chloro-5-hydroxymethyl-1H-imidazol-1-yl)methyl]quinolin-2-yl}benzoate 174 mg (0.376 mmol) of methyl 2-{6-[(2-butyl-4-chloro-5-hydroxymethyl-1H-imidazol-1-yl)methyl]quinolin-2-yl}benzoate obtained in Example 3 were mixed with 30.0 mg (0.751 mmol) of sodium hydroxide, 32 ml of water and 3 ml of ether and the mixture was stirred at room temperature for 24 hours. After concentrated under reduced pressure, the concentrate was partitioned between water and ether. The aqueous layer was acidified with 1N hydrochloric acid and extracted with ethyl acetate. The organic layer was dried over magnesium sulfate followed by filtration. The resulting filtrate was concentrated under reduced pressure to obtain 134 mg of 2-{6-[(2-butyl-4-chloro-5-hydroxymethyl-1H-imidazol-1-yl)methyl]quinolin-2-yl}benzoic acid.

The thus obtained product was dissolved in an equivalent amount (0.297 mmol) of a 1N sodium hydroxide solution and then lyophilized. Thus, 130 mg of sodium 2-{6-[(2-butyl-4-chloro-5-hydroxymethyl-1H-imidazol-1-yl)methyl]-quinolin-2-yl}benzoate was obtained.
NMR (270 MHz, D$_2$O):

δ7.4–8.2 (m, 9H); 5.5 (s, 2H); 4.6 (s, 2H); 2.8 (t, J=8 Hz, 2H); 2.0 (t, J=3 Hz, 1H); 1.5 (m, 2H); 1.2 (m, 2H); 0.8 (t, J=7 Hz, 3H)

EXAMPLE 5

Synthesis of methyl 6-[(2-butyl-4-chloro-5-formyl-1H-imidazol-1-yl)methyl]-2-(2-methoxycarbonylphenyl)-4-quinolinecarboxylate To 540 mg (1.610 mmol) of methyl 2-(2-methoxycarboxylphenyl)-6-methyl-4-quinolinecarboxylate obtained in Reference Example 3 were added 4 ml of carbon tetrachloride and then 315 mg (1.77 mmol) of N-bromosuccinic acid imide and 8.7 mg (0.053 mmol) of azobisisobutyronitrile. The mixture was heated under reflux for one hour and concentrated under reduced pressure. The residue was dissolved in dichloromethane and washed with water. The organic layer was dried over magnesium sulfate and filtered. The filtrate was concentrated under reduced presuure.

The thus obtained residue was dissolved in 2 ml of N,N-dimethylformamide. To the solution were added 44.6 mg (0.239 mmol) of 2-butyl-4-chloro-1H-imidazol-5-carbaladehyde and 36.3 mg of potassium carbonate. The resulting mixture was stirred at room temperature for 24 hours followed by filtration. The filtrate was concentrated under reduced pressure and the residue was purified by flash silica gel chromatography using a mixed solvent of hexane and ethyl acetate (5/1 to 4/1) to obtain 65.5 mg of methyl 6-[(2-butyl-4-chloro-5-formyl-1H-imidazol-1-yl)methyl]-2-(2-methoxy-carbonylphenyl)-4-quinolinecarboxylate.
NMR (270 MHz, CDCl$_3$):

δ9.8 (s, 1H); 7.5–8.5 (m, 8H); 5.8 (s, 2H); 4.0 (s, 3H); 3.6 (s, 3H); 2.7 (t, J=8 Hz, 2H); 1.7 (m, 2H); 1.4 (m, 2H); 0.8 (t, J=7 Hz, 3H)

EXAMPLE 6

Synthesis of methyl 6-[(2-butyl-4-chloro-5-hydroxymethyl-1H-imidazol-1-yl)methyl]-2-(2-methoxycarbonylphenyl)-4-quinolinecarboxylate 65.5 mg (0.126 mmol) of methyl 6-[(2-butyl-4-chloro-5-formyl-1H-imidazol-1-yl)methyl]-2-(2-methoxycarbonylphenyl-4 -quinolinecarboxylate obtained in Example 5 were dissolved in a mixed solvent of 2 ml of tetrahydrofuran and 2 ml of methanol and the mixture was stirred. After adding 5.24 mg (0.139 mmol) of sodium borohydride, the reaction mixture was allowed to react at room temperature for one hour. Then, the reaction mixture was concentrated under reduced pressure and dichloromethane was added to the residue followed by washing with a saturated sodium chloride solution. The organic layer was dried over magnesium sulfate and filtered. The filtrate was concentrated under reduced pressure to obtain 50.6 mg of methyl 6-[(2-butyl-4-chloro-5-hydroxymethyl-1H-imidazol-1-yl)methyl]-2-(2-methoxycarbonyl-phenyl)-4-quinolinecarboxylate.
NMR (270 MHz, CDCl$_3$):

δ7.4–8.4 (m, 8H); 5.4 (s, 2H); 4.5 (bs, 2H); 4.0 (s, 3H); 3.6 (s, 3H); 2.8 (bs, 1H); 2.6 (t, J=8 Hz, 2H); 1.6 (m, 2H); 1.3 (m, 2H); 0.8 (t, J=7 Hz, 3H)

EXAMPLE 7

Synthesis of 6-[(2-butyl-4-chloro-5-hydroxymethyl-1H-imidazol-1-yl)methyl]-2-(2-carboxyphenyl)-4-quinoline-carboxylic acid 50.6 mg (0.0969 mmol) of methyl 6-[(2-butyl-4-chloro-5-hydroxymethyl-1H-imidazol-1-yl)methyl]-2-(2-methoxycarbonylphenyl)-4-quinolinecarboxylate obtained in Example 6 were mixed with 33.5 mg (0.388 mmol) of sodium hydroxide, 1 ml of water and 0.3 ml of ethanol and the mixture was stirred at room temperature for 24 hours. After concentrated under reduced pressure, the concentrate was partitioned between water and ether. The aqueous layer was acidified with 1N hydrochloric acid and extracted with ethyl acetate to obtain 44.2 mg of 6-[(2-butyl-4-chloro-5-hydroxyethyl-1H-imidazol-1-yl)methyl]-2-(2-carboxyphenyl)-4-quinolinecarboxylic acid.

NMR (270 MHz, CD₃OD):

δ 7.6–8.6 (m, 8H); 5.6 (s, 2H); 4.6 (s, 2H); 2.7 (t, J=8 Hz, 2H); 1.6 (m, 2H); 1.4 (m, 2H); 0.9 (m, 3H)

EXAMPLE 8

Synthesis of 2-butyl-4-chloro-1-{[2-[2-[2-(triphenylmethyl)-2H-tetrazol-5-yl]phenyl]quinolin-6-yl]methyl}-1H-imidazole-5-carbaldehyde 1.36 g (2.56 mmol) of 5-[2-(6-methylquinolin-2-yl)phenyl]-2-triphenylmethyl-2H-tetrazole obtained in Reference Example 9 were treated in the same manner as in Example 1 to obtain 1.42 g of 2-butyl-4-chloro-1-{[2-[2-[2-(triphenylmethyl)-2H-tetrazol-5-yl]phenyl]quinolin-6-yl]methyl}-1H-imidazole-5-carbaldehyde.
NMR (270 MHz, CDCl₃):

δ 9.7 (s, 1H); 6.8-8.4 (m, 24H); 5.7 (s, 2H); 2.6 (m, 2H); 1.6 (m, 2H); 1.4 (m, 2H); 0.9 (t, J=7 Hz, 3H)

EXAMPLE 9

Synthesis of 2-butyl-4-chloro-1-{[2-[2-(1H-tetrazol-5-yl)phenyl]quinolin-6-yl]methyl}-1H-imidazole-5-carbaldehyde 0.70 g (0.98 mmol) of 2-butyl-4-chloro-1-{[2-[2-[2-(triphenylmethyl)-2H-tetrazol-5-yl]phenyl]quinolin-6-yl]methyl}-1H-imidazole-5-carbaldehyde obtained in Example 8 was suspended in 12 ml of methanol. 12 ml of concentrated hydrochloric acid was added thereto while in an iced water bath followed by stirring at room temperature for 24 hours. The reaction mixture was iced and alkalized with a 10N sodium hydroxide solution. After adding 10 ml of water thereto, the mixture was filtered and the filtered cake was washed with 10 ml of a 1N sodium hydroxide solution. The filtrate was acidified by adding concentrated hydrochloric acid dropwise thereto and extracted with 100 ml of ethyl acetate. The organic layer was dried over magnesium sulfate and filtered. The filtrate was concentrated to obtain 0.102 g of 2-butyl-4-chloro-1-{[2-[2-(1 H-tetrazol-5-yl)phenyl]-quinolin-6-yl]methyl}-1H-imidazole-5-carbaldehyde.
NMR (270 MHz, Acetone-d₆):

δ 9.8 (s, 1H); 7.2-8.3 (m, 9H); 5.8 (s, 2H); 2.3 (m, 2H); 1.7 (m, 2H); 1.4 (m, 2H); 0.9 (t, J=7 Hz, 3H)

EXAMPLE 10

Synthesis of {2-butyl-4-chloro-1-{[2-[2-(2-(triphenylmethyl)-2H-tetrazol-5-yl)phenyl]quinolin-6-yl]methyl}-1H-imidazol-5-yl}methanol 0.72 g (1.01 mmol) of 2-butyl-4-chloro-1-{[2-[2-[2-(triphenylmethyl)-2H-tetrazol-5-yl]phenyl]quinolin-6-yl]methyl}-1H-imidazole-5-carbaldehyde obtained in Example 8 was treated in the same manner as in Example 3 to obtain 0.70 mg of {2-butyl-4-chloro-1-{[2-[2-(2-(triphenylmethyl)-2H-tetrazol-5-yl)phenyl]quinolin-6-yl]methyl}-1H-imidazol-5-yl}-methanol.
NMR (270 MHz, CDCl₃):

δ 6.7-8.4 (m, 24H); 5.3 (s, 2H); 4.4 (d, J=6 Hz, 1H); 2.7 (m, 2H); 1.7 (m, 2H); 1.3 (m, 2H); 0.9 (t, J=7 Hz, 3H)

EXAMPLE 11

Synthesis of {2-butyl-4-chloro-1-{[2-[2-(1H-tetrazol-5-yl)phenyl]quinolin-6-yl]methyl}-1H-imidazol-5-yl}methanol 0.70 g (0.98 mmol) of {2-butyl-4-chloro-1-{[2-[2-(2-(triphenylmethyl)-2H-tetrazol-5-yl)phenyl]quinolin-6-yl]-methyl}-1H-imidazol-5-yl}methanol obtained in Example 10 was treated in the same manner as in Example 9 to obtain 95 mg of {2-butyl-4-chloro-1-{[2-[2-(1H-tetrazol-5-yl)phenyl]quinolin- -yl]methyl}-1H-imidazol-5-yl}methanol.
NMR (270 MHz, Acetone-d6):

δ 7.2–8.3 (m, 9H); 5.6 (s, 2H); 4.7 (s, 2H); 2.8 (m, 2H); 1.7 (m, 2H); 1.4 (m, 2H); 0.9 (t, J=7 Hz, 3H)

EXAMPLE 12

Synthesis of methyl 2-{6-[(2-ethyl-5,7-dimethyl-3H-imidazo-[4,5-b]pyridin-3-yl)methyl]quinolin-2-yl}benzoate To 154 mg (0.554 mmol) of methyl 2-(6-methylquinolin-2-yl)benzoate obtained in Reference Example 5 were added 2 ml of carbon tetrachloride and then 98.7 mg (0.554 mmol) of N-bromosuccinic acid imide and 4.55 mg (0.0277 mmol) of azobisisobutyronitrile. The mixture was heated under reflux for one hour. After the mixture was concentrated under reduced pressure, the residue was dissolved in dichloromethane and washed with water. The organic layer was dried over magnesium sulfate and filtered. The filtrate was concentrated under reduced pressure and the residue was dissolved in 1 ml of N,N-dimethylformamide. Separately, 71.1 mg (0.406 mmol) of 2-ethyl-5,7-dimethyl-3H-imidazo[4,5-b]pyridine was dissolved in 1 ml of dimethylformamide, 16.2 mg (0.406 mmol) of sodium hydride was added thereto and the mixture was stirred for 30 minutes. To this mixture was added the solution as prepared above followed by stirring for 24 hours.

Then, the mixture was concentrated under reduced pressure and the residue was extracted with ethyl acetate and washed twice with 20 ml of water. Magnesium sulfate was added to the organic layer, which was allowed to stand for 30 minutes. After filtration, the filtrate was concentrated. The thus obtained residue was purified by flash silica gel chromatography using a mixed solvent of hexane and ethyl acetate (2/3) to obtain 148 mg of methyl 2-{6-[2-ethyl-5,7-dimethyl-3H-imidazo[4,5-b]pyridin-3-yl)methyl]quinolin-2-yl}benzoate.
NMR (270 MHz, CDCl₃):

δ 6.94–8.08 (m, 10H); 5.66 (s, 2H); 3.63 (s, 3H); 2.83 (q, J=7.5 Hz, 2H); 2.70 (s, 3H); 2.61 (s, 3H); 1.34 (t, J=7.5 Hz, 3H)

EXAMPLE 13

Synthesis of sodium 2-{6-[(2-ethyl-5,7-dimethyl-3H-imidazo-[4,5-b]pyridin-3-yl)methyl]quinolin-2-yl}benzoate 116.9 mg (0.260 mmol) of methyl 2-{6-[2-ethyl-5,7-dimethyl-3H-imidazo[4,5-b]pyridin-3-yl)methyl]quinolin-2-yl}benzoate obtained in Example 12 were mixed with 31.1 mg (0.778 mmol) of sodium hydroxide, 2 ml of water and 2 ml of ethanol and the mixture was stirred at room temperature for 24 hours.

Then, the mixture was concentrated under reduced pressure and the concentrate was partitioned between water and ether. The aqueous layer was adjusted to pH 5 with 1N hydrochloric acid and extracted with ethyl acetate. The organic layer was dried over magnesium sulfate and filtered. The filtrate was concentrated under reduced pressure to obtain 46.0 mg of 2-{6-[(2-ethyl-5,7-dimethyl-3H-imidazo [4,5-b]pyridin-3-yl)methyl]quinolin-2-yl}benzoic acid. The thus obtained product was mixed with water and a 1N sodium hydroxide solution which were added in an equivalent amount (0.105 mmol). The resulting solution was lyophilized to obtain 43.6 mg of sodium 2-{6-[(2-ethyl-5,7-dimethyl-3H-imidazo[4,5-b]pyridin-3-yl)methyl]quinolin-2-yl}benzoate.
NMR (270 MHz, D₂O):

δ6.89–8.00 (m, 10H); 5.50 (s, 2H); 2.79 (q, J=7.6 Hz; 2H); 2.49 (s, 3H); 2.41 (s, 3H); 1.17 (t, J=7.6 Hz, 3H)

EXAMPLE 14

Synthesis of 2-ethyl-5,7-dimethyl-3-{[2-[2-(2-(triphenyl-methyl)-2H-tetrazol-5-yl)phenyl]quinolin-6-yl]methyl}-3H-imidazo[4,5-b]pyridine To 1.36 g (2.56 mmol) of 5-[2-(6-methylquinolin-2-yl)phenyl]-2-triphenylmethyl-2H-tetrazole obtained in Reference Example 9 were added 13 ml of carbon tetrachloride followed by stirring, and then 0.46 g (2.46 mmol) of N-bromosuccinimide and 21 mg (0.128 mmol) of azobisisobutylonitrile. The mixture was heated under reflux for 3 hours, allowed to cool and concentrated. The residue was partitioned between 40 ml of methylene chloride and 40 ml of water. The organic layer was dried over magnesium sulfate and filtered. The filtrate was concentrated and the concentrate was purified by flash silica gel chromatography using a mixed solvent of hexane and ethyl acetate (2/3) to obtain 0.86 g of 2-ethyl-5,7-dimethyl-3-{[2-[2-(2-(triphenyl-methyl)-2H-tetrazol-5-yl)phenyl]quinolin-6-yl]methyl}-3H-imidazo[4,5-b]pyridine.
NMR (270 MHz, CDCl₃):

δ6.8–8.2 (m, 25H); 5.04 (s, 2H); 2.76 (q, J=7.5 Hz, 2H); 2.68 (s, 3H); 2.6 (s, 3H); 1.28 (t, J=7.5 Hz, 3H)

EXAMPLE 15

Synthesis of 2-ethyl-5,7-dimethyl-3-{[2-[2-(1H-tetrazol-5-yl)phenyl]quinolin-6-yl]methyl}-3H-imidazo[4,5-b]pyridine 852 mg (1.21 mmol) of 2-ethyl-5,7-dimethyl-3-{[2-[2-(2-(triphenylmethyl)-2H-tetrazol-5-yl)phenyl]quinolin-6-yl]methyl}-3H-imidazo[4,5-b]pyridine obtained in Example 14 were suspended in 12 ml of methanol and 12 ml of concentrated hydrochloric acid were added thereto over an iced water bath. After stirring at room temperature for 24 hours, the reaction mixture was cooled with ice and acidified with a 10 N sodium hydroxide solution. 10 ml of water was added thereto followed by filtration and the filter cake were washed with 10 ml of a 1N sodium hydroxide solution. The filtrate was acidified by adding concentrated hydrochloric acid dropwise thereto with stirring and then extracted with 100 ml of ethyl acetate. The organic layer was dried over magnesium sulfate and filtered. The filtrate was concentrated to obtain 518 mg of 2-ethyl-5,7-dimethyl-3-{[2-[2-(1H-tetrazol-5-yl)phenyl]quinolin-6-yl]methyl}-3H-imidazo[4,5-b]pyridine.
NMR (270 MHz, CD₃OD):

δ7.2–8.3 (m, 10H); 5.84 (s, 2H); 2.99 (q, J=7.5 Hz, 1H); 2.73 (s, 3H); 2.67 (s, 3H); 1.36 (t, J=7.5 Hz, 3H)

EXAMPLE 16

Synthesis of methyl 2-{6-[(2-butyl-3H-imidazo[4,5-b]pyridin-3-yl)methyl]quinolin-2-yl}benzoate The procedure of Example 12 was repeated except that using 0.60 g (3.44 mmol) of 2-butyl-1H-imidazo[4,5-b]pyridine in place of 2-ethyl-5,7-dimethyl-1H-imidazo[4,5-b]pyridine to obtain 0.68 g of methyl 2-{6-[(2-butyl-3H-imidazo[4,5-b]pyridin-3-yl)methyl]quinolin-2-yl}benzoate.
NMR (270 MHz, CDCl₃):

δ7.2–8.4 (m, 12H); 5.7 (s, 2H); 3.62 (s, 3H); 2.85 (t, J=7.6 Hz, 2H); 1.83 (m, 2H); 1.41 (m, 2H); 0.9 (t, 7.3 Hz, 3H)

EXAMPLE 17

Synthesis of sodium 2-{6-[2-butyl-3H-imidazo[4,5-b]pyridin-3-yl)methyl]quinolin-2-yl}benzoate 0.68 g (1.52 mmol) of methyl 2-(6-[(2-butyl-3H-imidazo[4,5-b]pyridin-3-yl)methyl]quinolin-2-yl}benzoate obtained in Example 16 was treated in the same manner as in Example 13 to obtain 0.47 g of sodium 2-{6-[2-butyl-3H-imidazo[4,5-b]pyridin-3-yl)methyl]quinolin-2-yl}benzoate.
NMR (270 MHz, D₂O):

δ7.2–8.1 (m, 12H); 5.12 (s, 2H); 2.69 (t, J=7.6 Hz, 2H); 1.49 (m, 2H); 1.15 (m, 2H); 0.68 (t, J=7.3 Hz, 3H)

EXAMPLE 18

Synthesis of methyl 2-{6-[2-propyl-3H-imidazo[4,5-b]pyridin-3-yl)methyl]quinolin-2-yl}benzoate The procedure of Example 12 was repeated except for using 0.47 g (2.92 mmol) of 2-propyl-1H-imidazo[4,5-b]pyridine in place of 2-ethyl-5,7-dimethyl-1H-imidazo[4,5-b]pyridine to obtain 0.64 g of methyl 2-{6-[2-propyl-3H-imidazo[4,5-b]pyridin-3-yl)methyl]quinolin-2-yl}benzoate.
NMR (270 MHz, CDCl₃):

δ7.2–8.4 (m, 12H); 5.7 (s, 2H); 3.62 (s, 3H); 2.84 (t, J=7.7 Hz, 2H); 1.89 (m, 2H); 1.0 (t, J=7.3 Hz, 3H)

EXAMPLE 19

Synthesis of sodium 2-{6-[2-propyl-3H-imidazo[4,5-b]pyridin-3-yl)methyl]quinolin-2-yl}benzoate 0.64 g (1.46 mmol) of methyl 2-{6-[2-propyl-3H-imidazo[4,5-b]pyridin-3-yl)methyl]quinolin-2-yl}benzoate obtained in Example 18 was treated in the same manner as in Example 13 to obtain 0.64 g of sodium 2-{6-[2-propyl-3H-imidazo[4,5-b]pyridin-3-yl)methyl]quinolin-2-yl}benzoate.
NMR (270 MHz, D₂O):

δ7.2–8.2 (m, 12H); 5.5 (s, 2H); 2.76 (t, J=7.8 Hz, 2H); 1.63 (m, 2H); 0.83 (t, J=7.3 Hz, 3H)

EXAMPLE 20

Synthesis of 2-ethyl-5,7-dimethyl-3-{[4-chloro-2-[2-(2-(triphenylmethyl)-2H-tetrazol-5-yl)phenyl]quinolin-6-yl]methyl}-3H-imidazo[4,5-b]pyridine 133 mg (0.236 mmol) of 5-[2-(4-chloro-6-methylquinolin-2-yl)phenyl]-2-(triphenylmethyl)-2H-tetrazole obtained in Reference Example 11were treated in the same manner as in Example 14 to obtain 57 mg of 2-ethyl-5,7-dimethyl-3-{[4-chloro-2-[2-(2-(triphenylmethyl)-2H-tetrazol-5-yl)phenyl]quinolin-6-yl]methyl}-3H-imidazo[4,5-b]pyridine.
NMR (270 MHz, CDCl₃):

δ6.8–8.2 (m, 24H); 5.7 (s, 2H); 2.8 (q, J=8 Hz, 2H); 2.7 (s, 3H); 2.6 (s, 3H); 1.4 (t, J=8 Hz, 3H)

EXAMPLE 21

Synthesis of 2-ethyl-5,7-dimethyl-3-{[4-chloro-2-[2-(1H-tetrazol-5-yl)phenyl]quinolin-6-yl]methyl}-3H-imidazo[4,5-b]pyridine 56 mg of 2-ethyl-5,7-dimethyl-3-{[4-chloro-2-[2-(2-(triphenylmethyl)-2H-tetrazol-5-yl)phenyl]quinolin-6-yl]

methyl}-3H-imidazo[4,5-b]pyridine obtained in Example 20 were treated in the same manner as in Example 15 to obtain 22 mg of 2-ethyl-5,7-dimethyl-3-{[4-chloro-2-[2-(1H-tetrazol-5-yl)phenyl]quinolin-6-yl]methyl}-3H-imidazo[4,5-b]pyridine.

NMR (270 MHz, CDCl$_3$):

δ7.2–8.0 (m, 8H); 6.9 (s, 1H); 5.6 (s, 2H); 2.8 (q, J=8 Hz, 4H); 2.6 (s, 3H); 2.5 (s, 3H); 1.3 (t, J=8 Hz, 3H)

EXAMPLES 22–48

The following compounds are synthesized in the same manner as described in the above Examples.

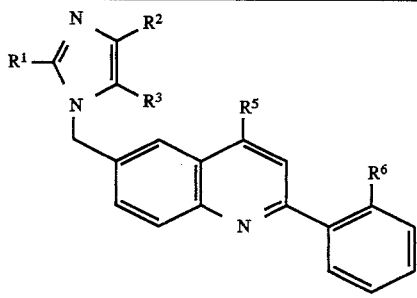

| Example No. | R$^1$ | R$^2$ | R$^3$ | R$^5$ | R$^6$ |
|---|---|---|---|---|---|
| Example 22 | n-Bu | Cl | CH$_2$OH | Cl | COONa |
| Example 23 | n-Bu | Cl | CH$_2$OH | Cl | tetrazole |
| Example 24 | n-Bu | Cl | COOH | H | COOH |
| Example 25 | n-pentyl | Cl | CH$_2$OH | H | tetrazole |
| Example 26 | n-pentyl | Cl | CH$_2$OH | COOH | COOH |
| Example 27 | n-pentyl | Cl | CH$_2$OH | Cl | COOH |
| Example 28 | n-pentyl | Cl | COOH | Cl | NHSO$_2$CF$_3$ |

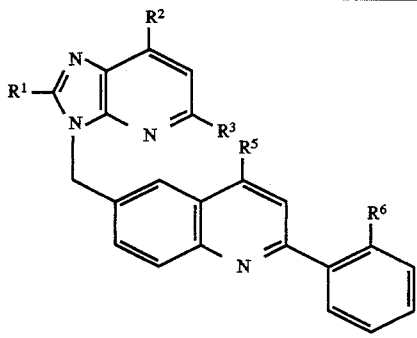

| Example No. | R$^1$ | R$^2$ | R$^3$ | R$^5$ | R$^6$ |
|---|---|---|---|---|---|
| Example 29 | Et | Me | Me | H | NHSO$_2$CF$_3$ |
| Example 30 | Et | Me | Me | Cl | COOH |
| Example 31 | Et | Me | Me | COOH | COOH |
| Example 32 | n-Pr | Me | H | H | COOH |
| Example 33 | n-Pr | Me | H | H | tetrazole |
| Example 34 | n-Pr | H | H | H | tetrazole |
| Example 35 | n-Bu | H | H | H | tetrazole |
| Example 36 | O-n-Pr | H | H | H | COOH |
| Example 37 | O-n-Pr | H | H | H | tetrazole |
| Example 38 | O-Et | Me | H | H | COOH |
| Example 39 | O-Et | Me | H | H | tetrazole |
| Example 40 | O-Et | Me | Me | H | COOH |
| Example 41 | O-Et | Me | Me | H | COOMe |
| Example 42 | O-Et | Me | Me | H | tetrazole |
| Example 43 | cyclopropyl | H | H | H | COOH |
| Example 44 | cyclopropyl | H | H | H | tetrazole |
| Example 45 | cyclopropyl | Me | H | H | COOH |
| Example 46 | cyclopropyl | Me | H | H | tetrazole |
| Example 47 | cyclopropyl | Me | Me | H | COOH |
| Example 48 | cyclopropyl | Me | Me | H | tetrazole |

NMR data for the representative compounds among the compounds of Examples 22 to 48 are given below.

EXAMPLE 22

2-butyl-1-[2-(2-carboxyphenyl)-4-chloroquinolin-6-yl]methyl-4-chloro-5-hydroxymethyl-1H-imidazole sodium salt NMR (270 MHz, D$_2$O):

δ7.4–8.0 (m, 8H); 5.5 (s, 2H); 4.6 (s, 2H); 2.8 (t, J=8.1 Hz, 2H); 2.0 (t, J=3.0 Hz, 1H); 1.5 (m, 2H); 1.2 (m, 2H); 0.8 (t, J=7.1 Hz, 3H)

EXAMPLE 25

5-hydroxymethyl-2-pentyl-1-{2-[2-(1H-tetrazol-5-yl)phenyl]quinolin-6-yl}methyl-1H-imidazole NMR (270 MHz, Acetone-d$_6$):

δ7.2–8.3 (m, 9H); 5.6 (s, 2H); 4.7 (s, 2H); 2.7 (t, J=7.1 Hz, 2H); 1.7 (m, 2H); 1.3 (m, 4H); 0.9 (t, J=7.1 Hz, 3H)

EXAMPLE 31

3-[2-(2-carboxyphenyl)-4-carboxylquinolin-6-yl]methyl-2-ethyl-5,7-dimethyl-3H-imidazo[4,5-b]pyridine NMR (270 MHz, CD$_3$OD):

δ7.2–8.3 (m, 9H); 5.6 (s, 2H); 2.9 (q, J=8.1 Hz, 2H); 2.6 (s, 3H); 2.5 (s, 3H); 0.7 (t, J=8.1 Hz, 3H)

EXAMPLE 35

2-butyl-3-{2-[2-(1H-tetraxol-5-yl)phenyl]quinolin-6-yl]methyl-3H-imidazo[4,5-b]pyridine NMR (270 MHz, Acetone-d$_6$):

δ6 7.1–8.3 (m, 12H); 5.6 (s, 1H); 2.7 (t, J=7.0 Hz, 2H); 1.5 (m, 2H); 0.8 (t, J=7.0 Hz, 3H)

EXAMPLE 38

3-[2-(2-carboxyphenyl)quinolin-6-yl]methyl-2-ethoxy-5-methyl-3H-imidazo[4,5-b]pyridine sodium salt NMR (270 MHz, D$_2$O):

δ6 7.2–8.2 (m, 11H); 5.5 (s, 2H); 4.0 (q, J=7.0 Hz, 2H); 2.5 (s, 3H); 1.4 (t, J=7.0 Hz, 3H)

EXAMPLE 40

3-[2-(2-carboxyphenyl)quinolin-6-yl]methyl-5,7-dimethyl-2-ethoxy-3H-imidazol[4,5-b]pyridine sodium salt NMR (270 MHz, D$_2$O):

δ7.2–8.2 (m, 10H); 5.5 (s, 2H); 4.0 (t, J=7.0 Hz, 2H); 2.6 (s, 3H); 2.5 (s, 3H); 1.4 (t, J=7.0 Hz, 3H)

EXAMPLE 45

3-[2-(2-carboxyphenyl)quinolin-6-yl]methyl-2-cyclopropyl-5-methyl-3H-imidazo[4,5-b]pyridine sodium salt NMR (270 MHz, D$_2$O):

δ5 7.2–8.2 (m, 12H); 5.5 (s, 2H); 4.0 (q, J=7.1Hz, 2H); 2.5 (s, 3H); 2.2 (m, 1H); 1.4 (t, J=7.1 Hz, 3H); 1.1 (m, 4H)

TEST EXAMPLE

Inhibition of binding of angiotensin II to rat smooth muscle cells

The compounds prepared in Examples 2, 4, 11, 12, 13, 15, 17 and 21 and $^{125}$I-Tyr$^4$-angiotensin II (0.25 µCi, 150 µl: NEX-105, NEX Co., hereinafter referred to as $^{125}$I-AII) were added to rat aorta-derived smooth muscle cells and incubated at room temperature for one hour. Unbound $^{125}$I-AII was washed away with phosphate-buffered saline (PBS) and radioactivity of $^{125}$I-AII bound to the cells was measured and inhibitory activity (IC$_{50}$) of the compounds of the present invention to the binding of angiotensin II to its receptor were calculated. The results are shown below.

| Compound | IC$_{50}$ (M) |
|---|---|
| Example 2 | $5.0 \times 10^{-8}$ |
| Example 4 | $9.2 \times 10^{-10}$ |
| Example 11 | $2.5 \times 10^{-9}$ |
| Example 12 | $4.4 \times 10^{-7}$ |
| Example 13 | $6.4 \times 10^{-9}$ |
| Example 15 | $9.4 \times 10^{-10}$ |
| Example 17 | $1.1 \times 10^{-11}$ |
| Example 21 | $7.7 \times 10^{-9}$ |

PREPARATION EXAMPLE 1

Tablets
(Composition)

| | | |
|---|---|---|
| (1) | 2-Ethyl-5,7-dimethyl-3-{[2-[2-1H-tetrazol-5-yl)phenyl]quinolin-6-yl]methyl}-3H-imidazo-[4,5-b]pyridine (Example 15) | 10 mg |
| (2) | Direct Tablet-making Powder No. 209 (Fuji Kagaku) | 46.6 mg |
| | Aluminium magnesium metasilicate | 20% |
| | Corn starch | 30% |
| | Lactose | 50% |
| (3) | Crystalline cellulose | 24.0 mg |
| (4) | Calcium carboxymethyl cellulose | 4.0 mg |
| (5) | Magnesium stearate | 0.4 mg |

The components (1), (3) and (4) which had been separately passed through a 100 mesh screen in advance were dried to reduce their moisture content to a predetermined level and then mixed, together with the component (2) which had also been dried in the same manner, according to the above mixing ratio using a mixer. The thus uniformly mixed powder was mixed with the component (5) and stirred for a short period of time (30 seconds), and the resulting powder was applied to a tablet making machine (punch: 6.3 mm in diameter, 6.0 mmR) to obtain a tablet preparation, each tablet being 85 mg in weight.

If necessary, the thus obtained tablets may be coated with a common enteric film coating such as polyvinylacetal diethylaminoacetate or a food coloring agent.

PREPARATION EXAMPLE 2

Capsules
(Composition)

| | | |
|---|---|---|
| (1) | 2-Ethyl-5,7-dimethyl-3-{[2-[2-1H-tetrazol-5-yl)phenyl]quinolin-6-yl]methyl}-3H-imidazo-[4,5-b]pyridine (Example 15) | 50 g |
| (2) | Lactose | 935 g |
| (3) | Magnesium stearate | 15 g |

The above components were weighed and mixed uniformly, and the resulting powder was packed in hard gelatin capsules in an amount of 200 mg per capsule.

PREPARATION EXAMPLE 3

Injections
(Composition)

| | | |
|---|---|---|
| (1) | Hydrochloride of 2-ethyl-5,7-dimethyl-3-{[2-[2-1H-tetrazol-5-yl)phenyl]quinoline-6-yl]-methyl}-3H-imidazo-[4,5-b]pyridine (Example 15) | 5 mg |
| (2) | Sucrose | 100 mg |
| (3) | Physiological saline | 10 ml |

The above mixture solution was filtered through a membrane filter and again subjected to sterile filtration. The thus obtained filtrate was dispensed aseptically into vials, the atmosphere in the vials was replaced with nitrogen gas and then the resulting vials were sealed to prepare intravenous injections.

While the invention has been described in detail and with reference to specific examples thereof, it will be apparent to one skilled in the art that various changes and modifications can be made therein without departing from the spirit and scope thereof.

What is claimed is:

1. A 2-(2-carboxyphenyl)-6-methyl-4-quinoline carboxylic acid compound of formula (4):

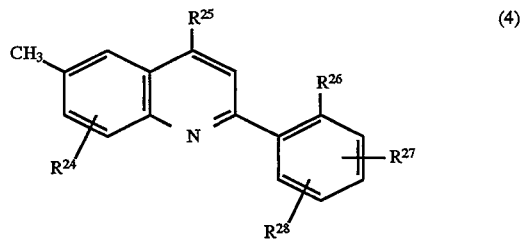

wherein R$^{25}$ is —COOH or —COOR$^{11}$; R$^{26}$ is —COOH or —COOR$^{12}$; R$^{24}$, R$^{27}$ and R$^{28}$ may be the same or different and each independently is a hydrogen atom, a halogen atom, a lower alkyl, alkoxy or C$_m$F$_{2m+1}$—group, wherein m is an integer of 1 to 6; and R$^{11}$ and R$^{12}$ are the same or different and each independently is a lower alkyl, alkenyl, cyclo lower alkyl, aryl or aralkyl group.

2. The compound of claim 1, wherein R$^{24}$, R$^{27}$ and R$^{28}$ each is a hydrogen atom; and R$^{11}$ and R$^{12}$ each is a lower alkyl group.

3. A process for producing a 2-(2-carboxyphenyl)-6-methyl-4-quinoline carboxylic acid compound of formula (4):

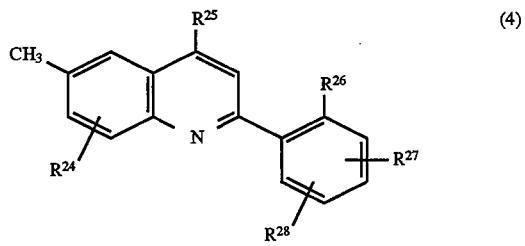

comprising reacting a 5-methylisatin compound of formula (5):

with a 2-acetyl benzoic acid compound of formula (6):

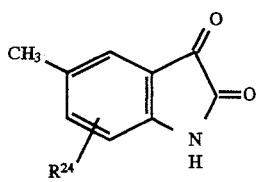

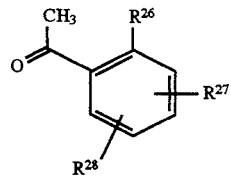

wherein $R^{25}$ is —COOH or —COOR$^{11}$; $R^{26}$ is —COOH or —COOR$^{12}$; $R^{24}$ $R^{27}$ and $R^{28}$ may be the same or different and each independently is a hydrogen atom, a halogen atom, a lower alkyl, alkoxy or $C_mF_{2m+1}$— group, wherein m is an integer of 1 to 6; and $R^{11}$ and $R^{12}$ are the same or different and each independently is a lower alkyl, alkenyl, cyclo lower alkyl, aryl or aralkyl group.

4. The process of claim 3, wherein said 5-methylisatin compound is 5-methylisatin, said 2-acetyl benzoic acid compound is 2-acetyl benzoic acid and said reaction product; 2-(2-carboxyphenyl)-6-methyl-4-quinoline carboxylic acid, is converted into an ester to give a compound of formula (4) in which $R^{11}$ and $R^{12}$ each is a lower alkyl group.

5. A process for producing a 2-(6-methylquinolin-2-yl) benzoic acid of formula (4):

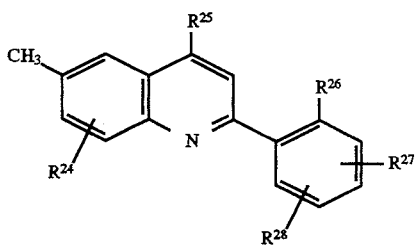

wherein $R^{25}$ is a hydrogen atom; $R^{26}$ is —COOR$^{12}$, $R^{24}$, $R^{27}$ and $R^{28}$ may be the same or different and each independently is a hydrogen atom, a halogen atom, a lower alkyl, alkoxy or $C_mF_{2m+1}$— group, wherein m is an integer of 1 to 6; and $R^{12}$ is a lower alkyl, alkenyl, cyclo lower alkyl, aryl or aralkyl group, comprising subjecting a 2-(2-carboxyphenyl)-6-methyl-4-quinoline carboxylic acid compound of formula (4) in which $R^{25}$ is —COOH and $R^{26}$ is —COOR$^{12}$ to decarboxylation by heating.

6. The process of claim 5, wherein $R^{24}$, $R^{27}$ and $R^{28}$ each is a hydrogen atom and $R^{12}$ is a lower alkyl group.

7. A process for producing a 2-(6-methylquinolin-2-yl) benzoic acid compound of formula (4):

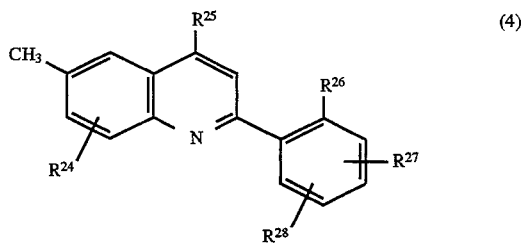

wherein $R^{25}$ is a hydrogen atom; $R^{26}$ is —COOR$^{12}$, $R^{24}$, $R^{27}$ and $R^{28}$ may be the same or different and each independently is a hydrogen atom, a halogen atom, a lower alkyl, alkoxy or $C_mF_{2m+1}$— group, wherein m is an integer of 1 to 6; and $R^{12}$ is a lower alkyl, alkenyl, cyclo lower alkyl, aryl or aralkyl group, comprising reacting a 5-methylisatin compound of formula ( 5 ):

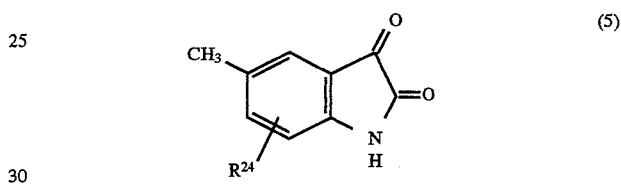

with a 2-acetyl benzoic acid compound of formula (6):

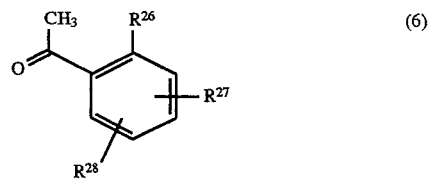

wherein $R^{26}$ is —COOH, thereby converting the resulting 2-(2-carboxyphenyl)-6-methyl-4-quinoline carboxylic acid compound of formula (4) in which $R^{25}$ and $R^{26}$ each is —COOH into a 2-(2-carboxyphenyl)-6-methyl-4-quinoline carboxylic acid compound of formula (4) wherein $R^{25}$ is —COOH and $R^{26}$ is —COOR$^{12}$; and subjecting the resulting compound to decarboxylation by heating.

8. The process of claim 7, wherein $R^{24}$, $R^{27}$ and $R^{28}$ each is a hydrogen atom and $R^{12}$ is a lower alkyl group.

* * * * *